United States Patent [19]

Wolz

[11] Patent Number: 6,074,690
[45] Date of Patent: Jun. 13, 2000

[54] METHOD FOR PRODUCING A SUPPORT STRUCTURE FOR INLAYS, CROWNS AND BRIDGES IN DENTISTRY

[76] Inventor: Stefan Wolz, Ludwig-Beckstrasse 57, D-68163 Mannheim, Germany

[21] Appl. No.: 09/155,312

[22] PCT Filed: Mar. 21, 1997

[86] PCT No.: PCT/DE97/00587

§ 371 Date: Sep. 25, 1998

§ 102(e) Date: Sep. 25, 1998

[87] PCT Pub. No.: WO97/35531

PCT Pub. Date: Oct. 2, 1997

[30] Foreign Application Priority Data

Mar. 25, 1996 [DE] Germany .................... 196 11 734

[51] Int. Cl.[7] ................ A61K 6/02; B22D 9/00; A61C 13/08
[52] U.S. Cl. ................ 427/2.29; 264/220; 264/16; 164/7.2
[58] Field of Search ................... 427/2.29, 190, 427/191, 205, 226; 264/19, 220, 317; 164/7.2, 516, 16, 125

[56] References Cited

U.S. PATENT DOCUMENTS

| 4,689,197 | 8/1987 | Groll et al. ................ 419/23 |
| 4,957,667 | 9/1990 | Hamer ........................ 264/16 |
| 5,024,711 | 6/1991 | Gasser et al. ................ 156/153 |
| 5,203,398 | 4/1993 | Easwaran ................ 164/516 |
| 5,702,514 | 12/1997 | Petticrew ................ 106/35 |

FOREIGN PATENT DOCUMENTS

WO 93/13727  7/1993  WIPO ................ A61C 5/08

*Primary Examiner*—Shrive Beck
*Assistant Examiner*—Jennifer Kolb
*Attorney, Agent, or Firm*—Foley & Lardner

[57] ABSTRACT

The invention concerns a process for the production of a frame for inlays, crowns and bridges in dental techniques. By means of the process, a considerable reduction in work and time expenditure is achieved in comparison with known processes. In the case of this process, frames of spinel, alumina, zirconia, metal powder or similar materials are produced in that a) a shrink foil is drawn on the stump or the stumps of a working model; b) the draw-non shrink foil is provided with a slip; and c) the shrink foil and the slip present on the shrink foil are removed from the working model and calcined to burn off the shrink foil.

9 Claims, No Drawings

METHOD FOR PRODUCING A SUPPORT STRUCTURE FOR INLAYS, CROWNS AND BRIDGES IN DENTISTRY

BACKGROUND OF THE INVENTION

In the case of the production of frames for inlays, crowns and bridges, processes are known which replace the previous metal cast frame with a frame of spinel, alumina or metal powder. Such a process, which uses spinel or alumina as material, is known under the name VITA In-Ceram®. Another process, in which metal powder is used, is known under the name DEGUSSA-Degusint®. Both processes consist of the following important steps:

a) From the model is produced a double, usually of silicone mass.

b) This double is poured out with a special gypsum and, after about 2 hours, a working model is removed from the mold.

c) The working model is dry ground, the preparation limit marked, and, in the case of In-Ceram, a sealant is applied, whereby, on the other hand, in the case of Degusint, a bonding agent is used.

d) In the case of Degusint, the working model is dried for 5 min at 700° C., subsequently preheated at 700° C. for 5 min, thereafter heated to 1100° C., and calcined for 2 min.

e) Slip or metal powder is applied to the sealed working model.

f) In the case of In-Ceram, the working model is usually kept for 6 hours at 120° C. and then heated to 1120° C. over 2 hours and kept for 2 hours.

g) After cooling, the In-Ceram is easily r(moved from the hollow space of the frame because of the gypsum shrinkage.

h) Thereafter follows the infiltration of the frame with glass powder, the calcining of the frame, and the usual finishing of the frame, such as grinding off of the edges, sand blasting and again calcining.

i) In the case of Degusint, the modelled tooth replacement is preheated to 700° C. in a graphite box for 10 min in an open oven chamber and thereafter sintered for 15 min at a temperature of 1090° C. (Degusint U) or 975° C. (Degusint G). After expiration of the sinter time, the graphite box is transferred immediately and without interruption into the vacuum box; the cooling time amounts to at least 15 min.

From the above description, it can be seen that this process is very time-and labor intensive. The expenditure of time for a frame amounts, in the case of the In-Ceram process, to about 14 hours and, in the case of Degusint, to about 4 hours.

BRIEF SUMMARY OF THE INVENTION

Inlays, crowns, and bridges for use in dental techniques are produced in accordance with the invention by drawing a shrink foil onto the stump or stumps of a working model, applying a slip onto the shrink foil, removing the shrink foil and the slip from the working model, and calcining the slip and the shrink foil, whereby the shrink foil burns off of the slip.

DETAILED DESCRIPTION OF THE INVENTION

Therefore, it is a task of the present invention to r educe the work and time expenditure in the case of the production of frames from spinel, alumina or metal powder. This task is accomplished by a process which includes the following process steps:

a) A foil is drawn onto the stump or the stumps of the working model.

b) The foil drawn onto the working model is provided with a slip or metal powder.

c) Finally, the foil, which has been provided with the slip or metal powder, is removed from the working model and calcined.

It can hereby be seen that the process provides considerable advantages. First of all, the doubling does not apply and thus the production of a second gypsum model is not needed. In the case of the production of bridges, the laborious surface grinding, sawing, and sticking of the working model onto an aluminium oxide bar does not take place. The 6 hours beating of a working model to 120° C. for the purpose of the removal of the moisture of the working model is also not necessary. Since, in the case of the process according to the invention, the foil is simply burnt, no special directions to heat up to the sinter temperature are necessary. On the other hand, in the case of the gypsum model according to the prior art, a heating up time of about 2 hours is needed in order to give the gypsum the possibility for shrinkage in order to be able to remove it from the frame.

Before the foil is shrunk onto the model, it is expedient to provide the stumps with a distance lacquer, which is again removed after the deep drawing.

Furthermore, it is advantageous to sandblast the foil after the deep drawing in order to improve the adhesion of the slip or metal powder if an already pre-treated foil is not used.

In the case of the production of bridge members, previously produced deep drawn shells can be fixed between two stumps which correspond in their form to the intermediate space.

In the case of application of the slip, these templates are filled with slip and thereby bound with the crowns.

In addition, it is also to be noted that, in principle, processes other than deep drawing are possible in order to achieve small caps of a desired layer thickness of 20–80 $\mu$m, preferably 30–50 $\mu$m.

The surface production of the foil can also take place by dipping into hot powder or by application of a wetting agent with subsequent dipping into powder. In both cases, the powder corresponds materially to the slip or metal powder.

A further advantage of the process according to the invention consists in that extremely different materials, such as metal oxides and sinter metal powder, can be worked up with the same process.

What is claimed is:

1. A method for the production of inlays, crowns and bridges in dental techniques by production of a frame from a slip material containing water and at least one of spinel, alumina, and zirconia comprising:

a) drawing a shrink foil on the stump or the stumps of a working model;

b) applying the slip onto the shrink foil;

c) removing the shrink foil and the slip present on the shrink foil from the working model; and d) calcining the slip and the shrink foil, whereby the shrink foil burns off of the slip.

2. The method according to claim 1, further comprising applying a distance lacquer to the stump or stumps.

3. The method according to claim 1, further comprising, before applying the slip, surface-treating the shrink foil.

4. The method according to claim 3, wherein surface-treating the shrink foil is accomplished by sandblasting.

5. The method according to claim 1, wherein the shrink foil is pre-treated shrink foil.

6. The method according to claim 3, wherein surface-treating the shrink foil is accomplished by dipping the shrink foil into hot powder which corresponds materially to the slip.

7. The method according to claim 3, wherein surface-treating the shrink foil is accomplished by providing the shrink foil with a wetting agent and subsequently dipping the shrink foil into a powder which corresponds materially to the slip.

8. The method according to claim 1, wherein drawing the shrink foil is accomplished by deep drawing.

9. The method according to claim 1, further comprising drying of the slip prior to removing the shrink foil and the slip from the working model.

\* \* \* \* \*